US011083694B2

(12) United States Patent
O'Mahony et al.

(10) Patent No.: US 11,083,694 B2
(45) Date of Patent: *Aug. 10, 2021

(54) INJECTABLE PHENOL FORMULATIONS AND METHODS OF THEIR USE

(71) Applicant: SAOL INTERNATIONAL DEVELOPMENT LTD., Hamilton (BM)

(72) Inventors: Leonard O'Mahony, Westmeath (IE); Sharon Hamm, Odessa, FL (US); John Devane, Dublin (IE); Imran Ahmed, Wilmington, NC (US); David Penake, Atlanta, GA (US)

(73) Assignee: SAOL INTERNATIONAL DEVELOPMENT LTD., Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 17/160,951

(22) Filed: Jan. 28, 2021

(65) Prior Publication Data
US 2021/0145766 A1 May 20, 2021

Related U.S. Application Data

(63) Continuation of application No. 16/776,184, filed on Jan. 29, 2020, now Pat. No. 10,959,962.

(60) Provisional application No. 62/806,188, filed on Feb. 15, 2019.

(51) Int. Cl.
*A61K 31/05* (2006.01)
*A61K 9/00* (2006.01)
*A61K 47/40* (2006.01)
*A61P 23/02* (2006.01)

(52) U.S. Cl.
CPC ............ *A61K 31/05* (2013.01); *A61K 9/0014* (2013.01); *A61K 9/0019* (2013.01); *A61K 47/40* (2013.01); *A61P 23/02* (2018.01)

(58) Field of Classification Search
CPC .................................................... A61K 31/05
See application file for complete search history.

(56) References Cited

U.S. PATENT DOCUMENTS

| 5,112,872 A | 5/1992 | Baba et al. |
|---|---|---|
| 7,964,644 B2 | 6/2011 | Meyer |
| 9,937,230 B2 | 4/2018 | Iadonato et al. |
| 10,314,739 B2 | 6/2019 | Allison et al. |
| 2003/0027833 A1* | 2/2003 | Cleary ................. A61K 31/245 514/270 |
| 2012/0190750 A1 | 7/2012 | Tseti |
| 2017/0209389 A1 | 7/2017 | Toth et al. |
| 2018/0147260 A1 | 5/2018 | Bright |

FOREIGN PATENT DOCUMENTS

| WO | 2013-078500 A1 | 6/2013 | |
|---|---|---|---|
| WO | WO-2013078500 A1 * | 6/2013 | ............. A61K 47/10 |

OTHER PUBLICATIONS

Braun et al., "Phenol Nerve Block in the Treatment of Acquired Spastic Hemiplegia in the Upper Limb", The Journal of Bone & Joint Surgery, vol. 55, No. 3, pp. 580-585 (1973).*
Arthur et al., "The Technology of In Vitro Staining of Nerves in Human Skin with Thiazin Dyes", The Journal of Investigative Dermatology, vol. 33, No. 3, pp. 121-144 (1959).*
Brewster ME et al., "Cyclodextrins as pharmaceutical solubilizers", Advanced Drug Delivery Reviews 59, 2007, pp. 645-666.
Bina Gidwani et al., "A Comprehensive Review on Cyclodextrin-Based Carriers for Delivery of Chemotherapeutic Cytotoxic Anticancer Drugs", BioMed Research International vol. 2015, Article ID 198268.
Brett Scott et al., "Intrathecal phenol and glycerin in metrizamide for treatment of intractable spasms in paraplegia", Journal of Neurosurgery, vol. 63, Issue 1, Jul. 1985, pp. 125-127.
Lin, S-Fen et al., "Complex Formation Between α-Cyclodextrin and 4-Substituted Phenols Studied by Potentiometric and Competitive Spectrophotometric Methods", Journal of Pharmaceutical Sciences, 72 (11), 1983, pp. 1333-1338.
Yin, Q. et al., "The quaternary lidocaine derivative QX-314 in combination with bupivacaine for long-lasting nerve block: Efficacy, toxicity, and the optimal formulation in rats", PLoS One, 12(3), e0174421, 2017, PP.
Wang, Z. et al., "Long-term effect of ropivacaine nanoparticles for sciatic nerve block on postoperative pain in rats", Int. J. Nanomed, 11, 2016, pp. 2081-2090.
Loyd DR et al., "Chen PB, Hargreaves KM. Anti-hyperalgesic effects of anti-serotonergic compounds on serotonin- and capsaicin-evoked thermal hyperalgesia in the rat", Neuroscience, Feb. 17, 2012, pp. 203:207-15.
Liu XJ et al., "Intraplantar injection of glutamate evokes peripheral adenosine release in the rat hind paw: involvement of peripheral ionotropic glutamate receptors and capsaicin-sensitive sensory afferents", J Neurochem, 80(4), Feb. 2002, pp. 562-570.
Lin CC et al., "Optimal effect of Phenol in Sciatic Nerve", Chinese Journal of Physiology, 58, 2015, pp. 237-243.
Szente, Lajos et al., "G.L. Spontaneous Opalescence of Aqueous-Cyclodextrin Solutions: Complex Formation or Self-Aggregation", Journal of Pharmaceutical Sciences,87(6), 1998, pp. 778-781.
International Search Report, WIPO Application No. PCT/US2020/015690, dated Apr. 28, 2020, English translation.
Bielen et al. "The Effect of a Cyclodextrin Vehicle on the Cardiovascular Profile of Propofol in Rats", Anesth. Analg., 1996, vol. 82, pp. 920-924. Abstract; p. 920, col. para 1; p. 920, col. 2, para 2; p. 921, col. 2, para 1.
McCrea et al. "Phenol Reduces Hypertonia and Enhances Strength: A Longitudinal Case Study", Neurorehabilitation and Neural Repair, 2004, vol. 18(2), pp. 112-116. p. 113, col. 1, para 3.

(Continued)

*Primary Examiner* — Kevin E Weddington
(74) *Attorney, Agent, or Firm* — Greenblum & Bernstein, P.L.C.

(57) ABSTRACT

Phenol formulations including phenol and an encapsulation agent, such as a cyclodextrin or derivatives thereof, and uses of such formulations.

19 Claims, 4 Drawing Sheets

(56) References Cited

OTHER PUBLICATIONS

Kenneth A. Connors, "The Stability of Cyclodextrin Complexes in Solution", Chemical Reviews, 1997, vol. 97, No. 5, pp. 1325-1357.
Kenneth A. Connors, "Prediction of Binding Constants of α-Cyclodextrin Complexes", Journal of Pharmaceutical Sciences vol. 85, No. 8, Aug. 1996, pp. 796-802.
Thomas W. Rosanske et al., "Stoichiometric Model of α-Cyclodextrin Complex Formation", Journal of Pharmaceutical Sciences vol. 69, No. 5, May 7980, pp. 564-567.
Kenneth A. Connors et al., "Theoretical Analysis of Comparative Studies of Complex Formation", vol. 55, No. 8, Aug. 1966, pp. 772-780.
Burnette et al., "Statistical Properties of Thermodynamic Quantities for Cyclodextrin Complex Formation" Journal of Pharmaceutical Sciences, vol. 89, No. 11, Nov. 2000, pp. 1389-1394.
Connors, "Population Characteristics of Cyclodextrin Complex Stabilities in Aqueous Solution", Journal of Pharmaceutical Sciences vol. 84, No. 7, Jul. 1995, pp. 843-848.
Wong et al., "Stability Constants for Complex Formation Between α-Cyclodextrin and Some Amines", Journal of Pharmaceutical Sciences vol. 72. No. 4. Apr. 1983, pp. 388-390.
Gadre et al., "Binding of Cyclodextrins to Alicyclic and Aromatic Substrates: Complex Formation of α-, β-, and γ-Cyclodextrins with Substituted Cyclohexanecarboxylic Acids and Phenylalkanoic Acids", Journal of Pharmaceutical Sciences vol. 86, No. 2, Feb. 1997, pp. 236-243.
Kenneth A. Connors et al., "Potentiometric Study of Molecular Complexes of Weak Acids and Bases Applied to Complexes of α-Cyclodextrin with para-Substituted Benzoic Acids", Journal of Pharmaceutical Sciences vol. 71, No. 2. Feb. 1982, p. 217-222.
Meng Xiao et al., "Effect of hydroxypropyl-β-cyclodextrin on the cometabolism of phenol and phenanthrene by a novel *Chryseobacterium* sp", Bioresource Technology 273 (2019), pp. 56-62.
Sevillano et al., "Feasibility study of degradation of phenol in a fluidized bed bioreactor with a cyclodextrin polymer as biofilm carrier", Biodegradation (2008) 19, pp. 589-597.
Guillaume et al., "Role of the Na+ ion on phenol derivatives/hydroxypropyl-β-cyclodextrin complex formation on porous graphitic carbon phase", Journal of Chromatography A, 955 (2002) pp. 197-205.
Ohara et al., "Selective Reimer-Tiemann Formylation of Phenol via Cyclodextrin Inclusion Complex" Pharmazie (Pharmacy) 33 (1978) 7, 467: Fac Pharm. Sc., Josai Univ., Sakado, Saitama, Japan; partial English translation.
Hu et al., "Solid-phase Microextraction of Phenol Compounds Using a Fused-Silica Fiber Coated with β-Cyclodextrin-bonded Silica Particles", Analytical Sciences Apr. 2004, vol. 20, 2004, pp. 667-671.
Dotsikas et al., "Efficient Determination and Evaluation of Model Cyclodextrin Complex Binding Constants by Electrospray Mass Spectrometry", J Am Soc Mass Spectrom 2003, 14, pp. 1123-1129.
Connors et al., "Effect of Cycloamyloses on Apparent Dissociation Constants of Carboxylic Acids and Phenols: Equilibrium Analytical Selectivity Induced by Complex Formation", vol. 65, No. 3, Mar. 1976, pp. 379-383.

\* cited by examiner

INJECTABLE PHENOL FORMULATIONS AND METHODS OF THEIR USE

CROSS-REFERENCE TO RELATED APPLICATIONS

This application claims the benefit of U.S. Provisional Application No. 62/806,188 filed Feb. 15, 2019, which is herein incorporated by reference in its entirety.

FIELD

This application relates to, among other things, injectable phenol formulations and their use.

BACKGROUND

Phenol is a carbolic acid, a derivative of benzene; a chemical with a wide variety of chemical and industrial applications (such as plastics and herbicides). Phenol is also a precursor agent to some pharmaceuticals, such as aspirin and has been used directly in medical applications ranging from local anesthetic effects to relief of skeletal muscle spasticity via motor nerve blockade.

Phenol is a tissue non-discriminatory protein denaturing chemical. When phenol comes in contact with protein rich tissues, it rapidly causes damage to the tissues and eventually leads to degeneration of the cells and protein structures, including nerves. Given this affect, intraneural and perineural injections of phenol have been used to cause neurolysis to treat a multitude of diseases and syndromes, including muscle spasticity and pain. Phenol has also been used as a non-discriminatory lysing agent for cysts, hemorrhoids, tumors and other syndromes requiring tissue ablation.

To obtain the desired clinical effects on skeletal muscle a phenol solution is typically injected perineurally to a target nerve, nerve complex, or nerve ending. Phenol chemically damages the nerve and interferes with nerve conduction. The application of phenol to nerves has been used effectively since the 1950s to treat skeletal muscle spasticity, however the product has not undergone formal safety and efficacy clinical trials, nor any formal regulatory approval process. As a result, phenol is typically prepared extemporaneously upon physician order through an institutional or third-party compounding pharmacy, as a 1-10% phenol (w/w %) aqueous or aqueous/glycerin solution, for clinical use.

Phenol however is a non-specific toxic agent that interacts and damages many tissues, not just nerves. This means that most tissues which come in contact with injected phenol can also be damaged. The current formulations of phenol, most often in aqueous or glycerol solutions, used clinically are solutions wherein drug that can quickly diffuse into adjacent muscle/blood vessel and other soft tissues near the target site of injection in the body.

SUMMARY

Provided is a novel formulation of phenol suitable for use in humans and animals that addresses the issue of the therapeutic index of phenol administered by injection. By "Therapeutic Index" we mean in particular the balance between the desired therapeutic effect (nerve block and associated effects on motor function) and the undesirable adverse effects on local tissues (especially local muscle and other soft tissue). The complex forming formulation includes cyclodextrin and phenol at dose levels generally ranging from about 30-90 mg/ml (about 3% to 9% by weight) phenol that allows for the application of phenol to be injected perineurally to the target nerve.

While the mechanism of action of the invention is not fully understood, it is possible that it involves encapsulation/complexation of all the phenol or a proportion thereof within an inclusion complex including cyclodextrins, which appears to reduce the immediately available free fraction of phenol, minimizing instantaneous local tissue exposure and potential systemic concentrations. The evidence does not seem to suggest that the cyclodextrins are improving the solubility of the phenol (which is what cyclodextrins are commonly used for). Based on our findings, it appears that too much complexation compromises efficacy and too little complexation may impair the safety profile as represented by necrosis of the peripheral muscle tissue around the target nerve injection site. Degeneration appeared microscopically as irregular myofiber size and shape with internalized nuclei, infiltrating macrophages, and increased size and number of satellite cells. Necrosis appeared microscopically as myofiber pallor, loss of differential staining, loss of myofiber nuclei (hypocellularity), and fragmentation of fibers. Thus, the complexation of phenol with a cyclodextrin appears to provide an unexpectedly good effect by reducing local tissue damage, while still allowing for the desired activity.

The term "complexation" is used herein to refer to the perceived interaction between the phenol and cyclodextrin (or derivative). It is not intended to precisely define the specific structure formed, or to limit the manner in which phenol/cyclodextrin interact with the tissue in the course of a treatment with the composition. The term "encapsulation" or "aggregation" or "inclusion complex" might also be used to describe the nature of the interaction.

The invention provides phenol formulations, including: phenol, a cyclodextrin or derivative thereof complexing at least a portion of the phenol, and at least one pharmacologically acceptable solvent. In some embodiments, the formulation is for injection, and in some embodiments, the formulation is for topical application.

The cyclodextrin may be, for example, hydroxypropyl-β-cyclodextrin (HP-β-CD). In some embodiments, the concentration of the hydroxypropyl-β-cyclodextrin is from about 10% to about 20% by weight (w/w) of the formulation, such as from about 12% to about 18% by weight (w/w) of the formulation. In some embodiments, the concentration of the phenol is from about 3% to about 9% by weight (w/w) of the formulation, such as about 6% by weight (w/w) of the formulation.

The invention also provides methods for creating a nerve-block in a mammal comprising administering an effective amount of a phenol formulation, the formulation including phenol, a cyclodextrin or derivative thereof complexing at least a portion of the phenol, and at least one pharmacologically acceptable solvent for administration. In some embodiments, the administering is by injection, and in some embodiments, the administering is by topical application.

The invention also provides methods for treating therapeutic, cosmetic, or tissue lysis condition in a patient in need thereof, by injecting into or applying in proximity of a physiological target area in proximity to or within a nerve, blood vessel, tumour, or tissue growth of the patient an effective amount of a phenol formulation, the formulation including phenol, a cyclodextrin or derivative thereof complexing at least a portion of the phenol, and at least one pharmacologically acceptable solvent for injection. In some embodiments, the phenol formulation includes from about 4% to about 9% by weight phenol, and from about 10% to about 20% by weight cyclodextrin or derivative.

The invention also provides methods of manufacturing a phenol composition for injection, by combining a cyclodextrin or derivative thereof with a pharmacologically acceptable solvent for injection, mixing the cyclodextrin or derivative thereof and the pharmacologically acceptable solvent for injection until the cyclodextrin is dissolved, and adding phenol and mixing the composition until the phenol is dissolved in the composition.

Additional features and advantages of the present disclosure will be set forth in part in the description that follows, and in part will be apparent from the description, or may be learned by practice of the present disclosure. The objectives and other advantages of the present disclosure will be realized and attained by means of the elements and combinations particularly pointed out in the description and claims.

The foregoing general description and the following detailed description are exemplary and explanatory only to provide a further explanation of the present disclosure and are not restrictive of the scope of the subject matter encompassed by the claims.

DETAILED DESCRIPTION

Figure 1:
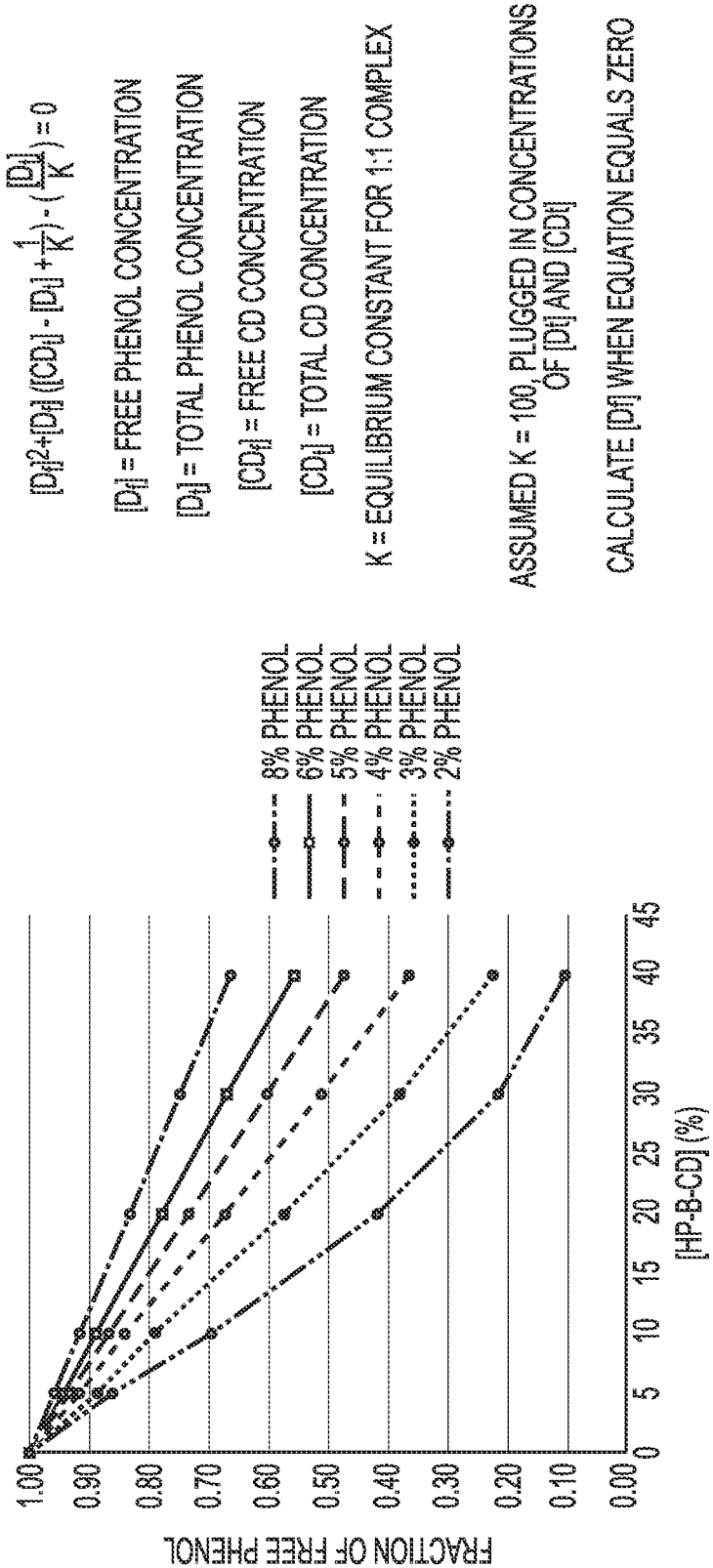
FIG. 1 shows the calculated degree of complexation of phenol based on the concentration of HP-β-CD used.

The particulars shown herein are by way of example and for purposes of illustrative discussion of the various embodiments of the present disclosure only, and provide what is believed to be the most useful and readily understood description of the principles and conceptual aspects of the disclosed subject matter. In this regard, no attempt is made to show details of the disclosed subject matter in more detail than is necessary for a fundamental understanding of the disclosure, the description making apparent to those skilled in the art how the several forms of the disclosure may be embodied in practice.

The following disclosure refers to more detailed embodiments, with occasional reference to the accompanying figures. The disclosed subject matter, however, may be embodied in different forms and should not be construed as limited to the embodiments set forth herein.

Unless otherwise defined, all technical and scientific terms used herein have the same meaning as commonly understood by one of ordinary skill in the art to which this disclosure belongs. The terminology used in the description herein is for describing particular embodiments only and is not intended to be limiting. As used in the specification and claims, the singular forms "a," "an," and "the" are intended to include the plural forms as well, unless the context clearly indicates otherwise. Also, the phrases "at least one" and "one or more" are intended to be interchangeable, and their use are not intended to limit the scope of any described or claimed feature preceded by "a," "an," and "the" to a singular form.

All publications, patent applications, patents, and other references mentioned herein are expressly incorporated by reference in their entirety, unless otherwise indicated.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by a particular embodiment. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosed subject matter are approximations, the numerical values set forth in the specific examples are reported as precisely as possible. Any numerical value, however, inherently contains certain errors necessarily resulting from the standard deviation found in the method used to obtain the value. Every numerical range given throughout this specification includes every narrower numerical range that falls within such broader numerical range, as if such narrower numerical ranges were all expressly written herein.

Reference to compounds in the specification includes esters and salts of such compounds. Thus, even if not explicitly disclosed, such esters and salts are contemplated and encompassed by reference to the compounds themselves.

All percent measurements in this application, unless otherwise stated, are measured by weight based upon 100% of a given sample weight. Thus, for example, 30% represents 30 weight parts out of every 100 weight parts of the sample.

The present disclosure relates, in part, to a composition comprising an active ingredient, and an agent for complexing the active ingredient. The composition may be a pharmaceutical composition.

A "pharmaceutical composition" as used herein means a composition comprising an active ingredient and at least one pharmaceutically acceptable excipient. As used herein, the term "pharmaceutically acceptable excipient" means a compound or ingredient that is compatible with the other ingredients in a pharmaceutical formulation and not injurious to an intended subject when administered in normal or therapeutically effective amounts. As used herein, an "intended subject" includes animals and/or humans. The terms "patient" and "subject" may be used interchangeably.

Suitable excipients are known to those of skill in the art and examples are described, for example, in the Handbook of Pharmaceutical Excipients (Kibbe (ed.), 3rd Edition (2000), American Pharmaceutical Association, Washington, D.C.), and Remington's Pharmaceutical Sciences (Gennaro (ed.), 20th edition (2000), Mack Publishing, Inc., Easton, Pa.), which, for their disclosures relating to excipients and dosage forms, are incorporated herein by reference. Examples of excipients include but are not limited to fillers, extenders, diluents, wetting agents, solvents, emulsifiers, preservatives, absorption enhancers, sustained-release matrices, starches, sugars, microcrystalline cellulose, granulating agents, lubricants, binders, disintegrating agents, coloring agents, release agents, coating agents, sweetening agents, flavoring agents, perfuming agents, antioxidants, plasticizers, gelling agents, thickeners, hardeners, setting agents, suspending agents, surfactants, humectants, carriers, stabilizers, and combinations thereof.

The present disclosure includes a large number and variety of components that are contemplated for inclusion in the pharmaceutical formulations. It should be recognized that when the inventors expressly contemplate including such components, they also expressly contemplate excluding such components. Thus, all components disclosed herein are expressly contemplated for exclusion as well.

As used herein, "active ingredient" is any component of the composition intended to furnish pharmacological activity or other direct effect in the diagnosis, cure, mitigation, treatment, or prevention of disease, or to affect the structure or any function of the body of the intended subject. Active ingredients include those components of the composition that may undergo chemical change during the manufacture of the composition and be present in a finished composition in a modified form intended to furnish the specified activity or effect. Active ingredients also include those components of the finished composition that during or after administration of the finished drug product to the intended user may undergo chemical change to a modified form intended to furnish the specified activity or effect. For example, the active ingredient can be a pharmaceutically acceptable salt of the component that furnishes the specified activity or effect.

As used herein, the term "pharmaceutically acceptable salt" includes salts that are physiologically tolerated by the intended subject. Such salts are typically prepared from an inorganic and/or organic acid. Examples of suitable inorganic acids include hydrochloric, hydrobromic, hydroiodic, nitric, sulfuric, and phosphoric acid. Organic acids may be aliphatic, aromatic, carboxylic, and/or sulfonic acids. Suitable organic acids include formic, acetic, propionic, succinic, camphorsulfonic, citric, fumaric, gluconic, lactic, malic, mucic, tartaric, para-toluenesulfonic, glycolic, glucuronic, maleic, furoic, glutamic, benzoic, anthranilic, salicylic, phenylacetic, mandelic, pamoic, methanesulfonic, ethanesulfonic, pantothenic, benzenesulfonic (besylate), stearic, sulfanilic, alginic, galacturonic, and the like.

As used herein, the term "prevent" or "prevention" in the context of treatment, for example, as in "preventing spasticity" or "prevention of spasticity" refers to a reduction in the spasticity. In other words, as used herein, "prevention" does not require 100% elimination of the symptom.

The composition may contain only one active ingredient, or more than one active ingredient, such as two, three, four, five, six, seven, eight, or nine active ingredients, or more than nine active ingredients.

The active ingredient can be selected from among active pharmaceutical ingredients (APIs). An API is a substance or mixture of substances intended to be used in the manufacture of a pharmaceutical product and that, when used in the production of a pharmaceutical product, becomes an active ingredient of the pharmaceutical product. Such substances are intended to furnish pharmacological activity or other direct effect in the diagnosis, cure, mitigation, treatment, or prevention of disease or to affect the structure or function of the body of the intended subject. In some embodiments, the active ingredient is phenol. In some embodiments, the active ingredient may be alcohol or another sclerosing agent. The active ingredient, such as phenol, can be in any form, such as liquid, granular, powder, or micronized form.

In addition to the active ingredient, the composition comprises a "complexing agent," such as a cyclodextrin or a derivative thereof. Cyclodextrins are cyclic oligosaccharides composed of a number of dextrose units of (α-1,4)-linked α-D-glucopyranose. The cyclodextrin structures contain a lipophilic central cavity and a hydrophilic outer surface. Cyclodextrins can have up to six, seven, eight, or more units (α-, β-, and γ-CDs have six, seven, and eight units, respectively). Cyclodextrins are known interact with hydrophobic drug molecules to form inclusion complexes and can be used to improve aqueous solubility. The structure of the three most common cyclodextrins are shown below for reference and understanding.

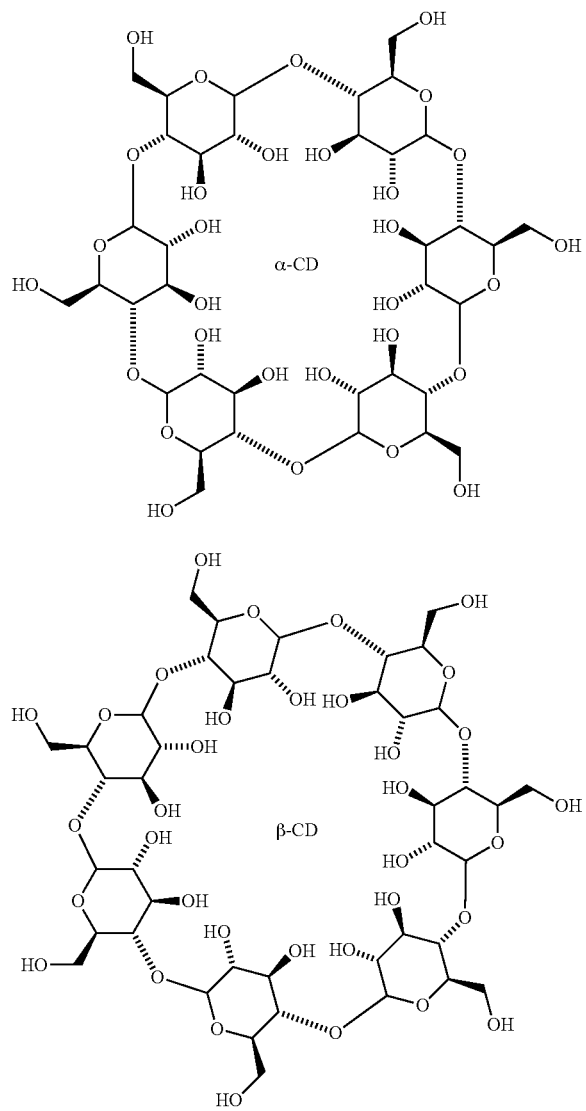

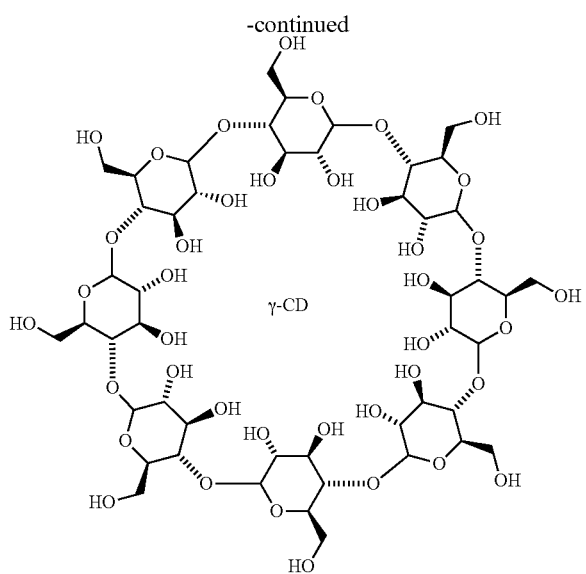

In the pharmaceutical industry, cyclodextrins have mainly been used as complexing agents to increase the aqueous solubility of active substances poorly soluble in water, in order to increase their bioavailability and to improve stability. In addition, cyclodextrins can be used to reduce or prevent gastrointestinal and ocular irritation, reduce or eliminate unpleasant smells or tastes, prevent drug-drug or drug-additive interactions within a formulation (all these properties are based on reduction of the free drug in solution), or to convert oils and liquid drugs into microcrystalline or amorphous powders. (Brewster Me. and Loftsson T (2007) Cyclodextrins as pharmaceutical solubilizers. Advanced Drug Delivery Reviews 59: 645-666.)

For β-cyclodextrin, which itself has a relatively low aqueous solubility, substitution of any of the hydrogen bond-forming hydroxyl groups, even by lipophilic functions, results in a dramatic improvement in the aqueous solubility of the derivative. Examples of β-CD derivatives used as excipients in medicines include, but are not limited to, the sulfobutyl ether of β-CD (SBE-β-CD), the hydroxypropyl derivative of β-CD (HP-β-CD), and the randomly methylated β-CD (RM-β-CD). The inventors contemplate the use of these cyclodextrin derivatives, or of any other cyclodextrin derivative that generally functions the same way in the disclosed compositions.

The term "complexing agent" (or "complexation agent") is used here to refer to the inventor-observed effect of the agent seemingly preventing the phenol in the formulation from being available for interacting with other components in the formulation, or with the surrounding tissue on injection of the formulation. This "complexing" effect appears to be based on an interaction between the complexing agent and the phenol, which complex does not appear to be caused by a covalent or ionic bond. However, some sort of lower energy bonding phenomena, such as hydrogen bonding, or hydrophobic interaction, may be taking place. This description does not in any way limit the invention, and is provided simply as a possible explanation for the phenomena observed.

In this invention, the complexing agent does not appear to render all molecules of the phenol permanently unavailable, or "bound." Thus, where the concentration of the phenol with respect to the complexation agent (i.e., the phenol:complexation agent ratio) is high, the "complexed" portion of phenol is lower. Where the phenol:complexation agent ratio is low, the "complexed" portion of phenol is higher. This observation is demonstrated in FIG. 1 for hydroxypropyl-beta-cyclodextrin ("HP-β-CD").

Each of the cyclodextrins shown above—α-, β-, and γ-CDs—are contemplated for use in the present invention. Additionally, derivatives of these molecules, examples of which are well known and commercially available, are also contemplated. A skilled person will be able to follow the present disclosure so as to be reproduce the invention using a variety of cyclodextrin derivatives.

In certain embodiments, only one of the noted cyclodextrins or its derivative is used, but combinations of various cyclodextrins may be used as well. Combinations may be useful, for example, to produce a more complex release/complexation profile, if desired. In this regard, each of the different cyclodextrins may have a different ideal complexation ratio, and by using combinations of different cyclodextrins, more complex release/complexation profiles may be achieved.

Embodiment compositions of the present invention may be intended for injection, and in those embodiments, other ingredients in the compositions may be selected based on their compatibility with other components and with the intended use. For example, a vehicle for use in injectable compositions may include water, or other pharmaceutically acceptable solvent. Water may be most preferable solvent in terms of its ease of use and patient compatibility, but the invention is not limited to the use of water, or even to aqueous solvents, and non-aqueous solvents are also contemplated. Topical formulations may include, for example, other excipients that are commonly used in topical formulations.

The dosage/concentration of the phenol in the inventive compositions is not critical, and may be adjusted as needed by the practitioner, based on observed results and intended use. Concentrations in the composition may be as low as, for example, 0.1 mg/ml, such as 0.2, 0.4, 0.6, 0.8, 1, 2, 5, 10, 20, 25, 30, 35, 40, 45, 50, 55, 60, 65, 70, 75, 80, or 85 mg/ml, or any number in between any of these values; concentrations may be as high as 900 mg/ml, such as 800, 700, 600, 500, 400, 300, 200, 150, 145, 140, 135, 130, 125, 120, 115, 110, 105, 100, 95, 90, 85, 80, 75, 70, 65, 60, 55, 50, 45, or 40 mg/ml, or any number in between any of these values. The concentration of phenol in a composition of the present invention is very easily adjusted and modified, and the inventors contemplate all concentrations between these upper and lower values—all possible fractional concentrations are not disclosed, as doing so would be unnecessary. Embodiments may range, for example, from about 30-90 mg/ml, or from about 40-80 mg/ml, or from about 50-70 mg/ml, or may be about 60 mg/ml.

Similarly, the concentration of the cyclodextrin and its derivatives (as complexing agent) may be adjusted as needed by the manufacturer or practitioner, based on observed results and intended use. Recognizing that the cyclodextrin and its derivatives interact with the phenol in the composition to modify its bioavailability, or release from the composition, the concentration of the cyclodextrin and its derivatives will be considered with that of the phenol so as to produce the desired result. Concentrations in the composition may be as low as, for example, 0.25 mg/ml, such as 0.5, 1, 1.5, 2, 2.5, 5, 12.5, 25, 50, 62.5, 75, 87.5, 100, 112.5, 125, 137.5, 150, 162.5, 175, 187.5, 200, or 212.5 mg/ml, or any number in between any of these values; concentrations may be as high as 1250 mg/ml, such as 750, 500, 375, 362.5, 350, 337.5, 325, 312.5, 300, 287.5, 275, 262.5, 250, 237.5, 225, 212.5, 200, 187.5, 175, 162.5, 150, 137.5, 125, 112.5, or 100 mg/ml, or any number in between any of these values. The concentration of cyclodextrin and its derivatives in a composition of the present invention is very easily adjusted and modified, and the inventors contemplate all concentrations between these upper and lower values—all possible fractional concentrations are not disclosed, as doing so would be unnecessary. Embodiments may range, for example, from about 100-200 mg/ml, or from about 125-175 mg/ml, or from about 140-160 mg/ml, or may be about 150 mg/ml.

Pharmaceutical compositions are typically provided in dosage forms that are suitable for administration to an intended subject by a desired route. Various dosage forms are described below, but are not meant to include all possible choices. One of skill in the art is familiar with the various dosage forms that are suitable for use, as described, for example, in Remington's Pharmaceutical Sciences, which has been incorporated by reference above. The most suitable route in any given case will depend on the nature and severity of the disease and/or condition being prevented, treated, and/or managed. For example, pharmaceutical compositions may be formulated for administration subcutaneously, intramuscularly, perineurally, intraneurally, transdermally, intraarticularly, intrathecally, intravenously, nasally, rectally, intravaginally, intracisternally, and topically.

Pharmaceutical compositions and dosage forms described herein may further comprise at least one additional active ingredient other than phenol. Such additional active ingredients may be included to treat, prevent, and/or manage the same condition being treated, prevented, and/or managed with phenol, or a different one. Alternatively, such additional pharmaceutical compounds may be provided in a separate formulation and co-administered to a subject or patient with the phenol according to the present disclosure. Such separate formulations may be administered before, after, or simultaneously with the administration of the phenol.

In some embodiments, the compositions of the invention will be stable at room temperature. As used herein, "stable" means capable of storage without significant alteration in the fundamental composition such that it remains usable as intended. In some embodiments, the compositions will be stable at room temperature; in some embodiments, the compositions will be stable under reduced temperature conditions, such as refrigeration or freezing. In some embodiments, the compositions are stable for one or more days, such as a week or month or more. In some embodiments, the compositions will include one or more additional ingredients to improve stability, such as antioxidants.

The compositions described above can be used in methods for treating, preventing, and/or managing various diseases and/or conditions, comprising administering to a subject or patient in need thereof a therapeutically effective amount of the phenol. The phrase "therapeutically effective amount" refers to the amount of the active ingredient (e.g., phenol), which alone or in combination with one or more other active ingredients, provides any therapeutic benefit in the prevention, treatment, and/or management of a particular diseases and/or condition.

Phenol is believed to act by impairing nerve conduction via nerve block. This can result in medical applications and cosmetic applications. Medical applications can range from local anesthetic to full nerve (motor and sensory) blocks that may be clinically beneficial in conditions such as pain, skeletal muscle spasticity and many others. The same mechanism allows phenol to be beneficial in cosmetic indications that smooth skin or reduce wrinkles. Finally, the lysing mechanism of phenol, unrelated to nerve block uses, may allow for clearance of unwanted tissue, tumor lysis, and removal of skin spots.

A particular aspect of the current invention relates to perineural injection of motor nerves that innervate major muscles that are subject to altered tone and associated spasticity in patients that have incurred traumatic brain injury, spinal cord injury or stroke. The same may be beneficial to patients with a variety of diseases, including multiple sclerosis, cerebral palsy, ALS, and many others.

Another particular aspect of the current invention relates to perineural or generally local injection of phenol to sensory nerves. The sensory nerve block may be beneficial in multiple pain syndromes such as osteoarthritis of the knee, post-knee replacement pain, cancer pain and neuralgias.

The inventors contemplate that a phenol formulation according to the invention may be used for any indication for which phenol is approved. Examples of contemplated indications include, but are not limited to, muscle spasticity of any origin or etiology, nerve pain, joint pain, cancer pain, osteoarthritic pain, cosmetic uses, local anesthesia, facet joint pain, discogenic pain, spinal stenosis, Sacro-Illiac joint dysfunction, lumbar spondylosis, migraine related pain, occipital neuralgia, osteosarcoma, soft-tissue sarcoma, ischemic leg pain, post-hip arthroplasty pain, post-knee replacement pain, focal hyperhidrosis, anismus, strabismus, hemifacial spasm, blepharospasm, cervical dystonia, spasmodic dysphonia, sialorrhea, gustatory sweating, facial rejuvenation, temporomandibular pain, peripheral nerve pain, post-herpetic neuralgia, trigeminal neuralgia, chronic migraine, glabellar lines, forehead ryetids, crow's feet, perioral lip lines, overactive bladder, upper limb spasticity, lower limb spasticity, carpal tunnel, fibromyalgia, rectal prolapse, post-surgical opioid reduction, Raynaud phenomenon, hot flashes, genodermatoses, hidradenitis superativa, pompholyx, eccrine nevus, pachynochia congenita, aquagenic keratoderma, androgenetic alopecia, psoriasis, darier disease, alopecia areata, hailey-hailey disease, linear IgA dermatosis, keloids, hypertrophic scars, hereditary spastic paraparesis, herpes zoster pain, radical mastectomy pain, complex regional pain syndrome, spastic diplegia, spastic quadriplegia, Morton's neuroma, post-amputation pain, phantom leg syndrome, hypoxic eschemic cepalopathy of prematurity, pilonidal sinus disease, neuromas, neuralgias, giant gastric leiomyomas, solid tumor devascularization, tumor ablation, herniotic groin pain, varicose veins, skin blemish removal, and wart removal.

The amount of the dose of the active ingredient administered, as well as the dose frequency, will vary depending on the particular dosage form used and route of administration. The amount and frequency of administration will also vary according to the age, body weight, and response of the individual subject or patient. Typical dosing regimens and locations can readily be determined by a competent physician without undue experimentation. It is also noted that the clinician or treating physician will know how and when to interrupt, adjust, or terminate therapy in conjunction with individual subject or patient response.

Changes to the efficacy and non-targeted tissue damage may be changed by increases or decreases in blood flow. The inventors contemplate that an increase in blood flow of local, non-targeted tissue may further enhance a reduction in tissue damage including but not limited to reduction in damage to the skin or skeletal muscle. This may be important for any application but particularly those in areas of sensitive or thin tissues such as the face, head, hand, feet or pubic regions for local therapeutic or cosmetic interventions. Changes in local blood flow could be created via any number of applications ranging from surface heating or cooling of the local area to injection of medications that change local blood flow.

The phenol formulation may be combined with dyes or other agents that support visualization of the site of application. Injectable versions of phenol may be localized with ultrasound, electronic stimulation, fluoroscopy or other potential visualization techniques. Dyes may also support visual localization of the phenol following application to the skin or direct injection while using cameras to support procedures.

The localization of the application, via injection or otherwise, may be desired to be more targeted in areas with complex soft-tissue structures in or near the targeted nerve or vein. In other potential uses, particularly those that are in close proximity to tissues such as bone like joint injections and benefit from blocking multiple nerves may benefit from the spreading effect that comes following injection of the phenol formulation. A physician or other skilled clinician, having read the present disclosure, will be able to readily determine the appropriate site of administration, as well as the dosing and frequency thereof. In this regard, it is not critical that the composition be injected directly into a nerve (as doing so can sometimes result in pain); rather, the composition can be injected or otherwise applied in a manner that it is applied to rather than into the nerve. Stated differently, the invention contemplates the application of the compositions directly or indirectly to nerve tissue.

Although typically physicians have avoided the use of phenol intravenously due to systemic exposure and toxicity concerns, this formulation may be used intravenously or intravascularly to cause localized vein sclerosis that may be useful in treatments of tumors, cancer or cosmetic applications like varicose veins.

Applications of the phenol formulation on moles or other skin spots may create a localized lysis to remove unwanted spots in a localized and non-surgical manner. A phenol formulation may also be used for topical use on a broader are of skin.

Typical single treatment, in potentially multiple injections or administrations, maximum doses of phenol may be up to 1 gram per treatment exposure. The formulation may allow for the use of phenol beyond 1 gram of daily systemic exposure and may provide for greater flexibility in frequency of exposure.

EXAMPLES

Example 1—Comparison of Various Strategies to Control Phenol Release

Phenol is useful in providing a nerve-blocking effect, but it is also generally toxic to mammalian tissue. The goal is to provide a composition that balances phenol's ability to provide useful nerve blockade, while minimizing local tissue destruction. With those competing interests in mind, this example explored three mechanistically different approaches to achieving the desired goal: 1) in situ gelling, 2) viscoelastic, and 3) complexation/encapsulation.

Example 1A—In Situ Gelling

In situ (thermo) gelling takes advantage of the ability of the gelling agent to react with, or change its behavior, after injection. The example tested here is poloxamer, which is believed to be capable of forming a gel within a certain concentration range at mammalian body temperature.

The inventors assessed thermo-gelling polymers comprising poloxamer 407 (P407), poloxamer 188 (P188) and/or combinations, to determine suitable thermogelling transition temperatures ($T_{sol\text{-}gel}$). Based on available literature, P407 has a narrow concentration range (16-20% w/w) in which $T_{sol\text{-}gel}$ is deemed acceptable; however a combination of P407 and P188 have been reported to be effective at increasing the range of viable concentrations by up regulating $T_{sol\text{-}gel}$ as well as improving the in situ dilutability of the gel.

In addition, determination of the phenol threshold levels was assessed to assess the impact of phenol on thermogelling properties of the optimal polymer/polymer blends. As phenol has the ability to hydrogen bond, there is potential for phenol to have a stabilizing/destabilizing effect.

A summary of the initial thermogelling properties of various compositions is shown in Table A below.

TABLE A

| Polymer Solutions (Poloxamer P407, P188) % w/w | Thermogelling transition temperatures ($T_{sol\text{-}gel}$) determined by Malvern Kinexus Rheometer |
| --- | --- |
| 5% P188 | No |
| 10% P188 | No |
| 15% P188 | No |
| 16% P407 | 29.42° C. |
| 18% P407 | 26.49° C. |
| 20% P407 | 24.35° C. |
| 10% P188 + 20% P407 | 38.49° C. |
| 15% P407 | 32.09° C. |
| 10% P188 + 16% P407 | No |

As can be seen in Table A above, poloxamer P188 at levels between 5-15% were not capable of generating a $T_{sol\text{-}gel}$ in the desired range of 29–36° C. The combination of P188 at 10% with P407 at different levels were not capable of generating a $T_{sol\text{-}gel}$ also. Poloxamer levels of P407 in the range of 15-16% was deemed to be the most suitable target with $T_{sol\text{-}gel}$ of 29.4-32.1° C.

Poloxamer solutions of P407 at 15-16% were assessed in combination with phenol at levels of 3-7.5%. Phenol was introduced into the P407 formulation in two different ways: (1) by addition of solid phenol fractionally, (2) solubilization of phenol in water and subsequent dropwise addition. In both cases, formulations gelled after addition of the phenol and remained gelled. It was noted that there was a solubility limit of phenol as phenol was not observed to dissolve >2% w/w in solution. In conclusion, the solubility limit of phenol is greatly impacting the ability to achieve the target 6% phenol levels in solution. Lower temperatures hinder the ability to achieve >3% phenol levels. The three-dimensional structure formed by P407 upon gelation at higher temperature is catalysed by phenol at room temperature. Phenol has a profound effect on poloxamer viscosity and resultant sol-gel transition.

In situ gelling with poloxamer did not appear to be a viable option based on the in vitro testing.

Example 1B—Viscoelastic Formulation

The second approach was to formulate the phenol with viscoelastic components, such as hyaluronic acid (HA), and sodium carboxymethyl cellulose (NaCMC), methylcellulose (MC), and PEG 3350, to determine if any would be an appropriate candidate. These polymers are widely used in the pharmaceutical industry and generally recognized as safe at concentrations that would be useful in the present formulations.

HA in particular is a well-known ubiquitous macromolecule found in vitreous body of eye, lubricant as synovial fluid in joints, and extracellular matrix of the skin. HA was initially selected, as it is a biodegradable, natural polymer with precedent of use in injectable formulations (EU-FLEXXA—sodium hyaluronate 1% in PBS). HA is used intraocularly as a viscoelastic during cataract extraction to protect corneal endothelium and is used as a dermal filler and intra-articularly as injections for synovial fluid replacement. The polymer was also considered for use as it may have potential to ameriolate the deleterious effect of phenol while preventing the formulation spread to peripheral tissues due to its favourable viscoelastic and biocompatible properties.

The following tests were performed: 1) 0.1/0.5/1.0% w/w HA with 6% w/w phenol formulation; 2) 0.5/1.0/2.0/3.0% w/w PEG 3350 with phenol; 3) blank MC formulations (0.1, 0.3, 0.5 and 1% w/w), and challenged 0.7% and 0.9% MC with 6% w/w phenol; 4) blank CMC-Na formulations (0.5, 1.0, 1.5 and 2% w/w), and challenged and characterized 0.5% and 0.7% MC with 6% w/w phenol.

A summary of the formulation finds is outlined in Table B.

TABLE B

| Sodium Hyaluronate (HA) | Carboxymethylcellulose | Methyl cellulose | Polyethylene glycol (PEG 3350) |
|---|---|---|---|
| Aqueous solutions exhibit non-Newtonian behavior (shear thinning) 1%, 2% and 3% HA formulations were too viscous to consider for further development 0.1% and 0.5% HA with 6% phenol have adequate viscosity and are free flowing solutions during withdrawal and injection | Aqueous solutions exhibit non-Newtonian behavior (shear thinning) 1%, 1.5% and 2% CMC-Na formulations were too viscous to consider for further development 0.5% and 0.7% CMC-Na with 6% phenol have adequate viscosity and are free flowing solutions during withdrawal and injection | Aqueous solutions exhibit non-Newtonian behavior (shear thinning) 0.1%, 0.3% and 0.5% MC formulations were not sufficiently viscous enough (<50 cP) for the viscoelastic approach. Formation of white precipitate after challenging 0.7% and 0.9% MC with 6% w/w phenol | PEG 3350 is approved in IM based formulations on the FDA IIG database upto 3% w/w Phase separation was observed in formulations with 0.5/1.0/2.0/3.0% w/w PEG 3350, 7.5% w/w Phenol. Cloudy solutions observed at 7.5% w/w phenol Solutions of PEG 3350 up to 5% were not deemed to be adequately viscous for this technology approach. |

Based on initial testing in vitro screening (evaluating viscosity, injectability, etc.), several HA and CMC formulations were selected for animal testing. The selected formulations and the justifications for their selection are shown in Table C below.

TABLE C

| Test Article | DESCRIPTION | POLYMER CONCENTRATION | VEHICLE | JUSTIFICATION |
|---|---|---|---|---|
| 1 | Sodium Hyaluronate 6% (60 mg/g) Phenol | 0.1% w/w | WFI | Lowest concentration evaluated for Na-HA that has zero shear viscosity ≥ 100 cP and passed syringeability test |
| 2 | Sodium Hyaluronate 6% (60 mg/g) Phenol | 0.5% w/w | WFI | Evaluated Concentration with highest viscosity to pass syringeability test |
| 3 | Carboxymethylcellulose sodium 6% (60 mg/g) Phenol | 0.5% w/w | WFI | Lowest concentration evaluated for CMC-Na that has zero shear viscosity ≥ 100 cP and passed syringeability test |
| 4 | Carboxymethylcellulose sodium 6% (60 mg/g) Phenol | 0.7% w/w | WFI | Evaluated Concentration with highest viscosity to pass syringeability test |

Table D below presents a summary of the histopathological data from the HA and CMC formulations noted above, and compared to phenol formulation as controls.

TABLE D

| Pathology | | Number of Animals | Group 1: Water for Injection | Group 2: 6% Aqueous Phenol (active control) | Group 3: 6% Phenol, 0.1% w/w sodium hyaluronate | Group 4: 6% Phenol, 0.5% w/w sodium hyaluronate | Group 5: 6% Phenol, 0.5% w/w carboxymethyl-cellulose sodium | Group 6: 6% Phenol, 0.7% w/w carboxymethyl-cellulose sodium |
|---|---|---|---|---|---|---|---|---|
| Sciatic Nerve degeneration | Total | | 0 | 10 | 8 | 8 | 3 | 3 |
| | 1> | | 0 | 2 | 6 | 7 | 2 | 2 |
| | 2> | | 0 | 6 | 2 | 0 | 1 | 0 |
| | 3> | | 0 | 2 | 0 | 1 | 0 | 1 |

TABLE D-continued

| Pathology | Number of Animals | Group 1: Water for Injection | Group 2: 6% Aqueous Phenol (active control) | Group 3: 6% Phenol, 0.1% w/w sodium hyaluronate | Group 4: 6% Phenol, 0.5% w/w sodium hyaluronate | Group 5: 6% Phenol, 0.5% w/w carboxymethyl-cellulose sodium | Group 6: 6% Phenol, 0.7% w/w carboxymethyl-cellulose sodium |
|---|---|---|---|---|---|---|---|
| Skeletal Muscle degeneration | Total | 4 | 10 | 10 | 7 | 7 | 4 |
|  | 1> | 4 | 5 | 5 | 4 | 4 | 3 |
|  | 2> | 0 | 5 | 5 | 3 | 3 | 1 |
| Necrosis | Total | 0 | 9 | 7 | 6 | 7 | 3 |
|  | 1> | 0 | 5 | 2 | 4 | 5 | 3 |
|  | 2> | 0 | 4 | 3 | 1 | 2 | 0 |
|  | 3> | 0 | 0 | 2 | 1 | 0 | 0 |
| Clinical Signs |  | No signs from 1-48 hours | 1 hr post dose: mild paresis (8/10), moderate paresis (2/10), decreased digit abduction (10/10) 4-48 hr post dose: mild paresis (9/10), moderate paresis (1/10), decreased digit abduction (10/10) | 1 hr post dose: mild paresis (8/10), moderate paresis (1/10), decreased digit abduction (9/10) 4 hr post dose: mild paresis (9/10), decreased digit abduction (9/10) 24 hr post dose: mild paresis (8/10), moderate paresis (1/10), decreased digit abduction (9/10) 48 hr post dose: mild paresis (9/10), decreased digit abduction (9/10) | 1 hr post dose: mild paresis (5/10), moderate paresis (2/10), decreased digit abduction (7/10) 4 hr post dose: mild paresis (7/10), decreased digit abduction (8/10) 24 hr post dose: mild paresis (6/10), moderate paresis (1/10), decreased digit abduction (8/10) 48 hr post dose: mild paresis (6/10), moderate paresis (1/10), decreased digit abduction (8/10) | 1 hr post dose: mild paresis (6/10), moderate paresis (1/10), decreased digit abduction (7/10), 4 hr post dose: mild paresis (7/10), decreased digit abduction (7/10) 24 hr post dose: mild paresis (6/10), decreased digit abduction (7/10) 48 hr post dose: mild paresis (6/10), decreased digit abduction (6/10) | 1 hr post dose: mild paresis (6/10), moderate paresis (3/10), decreased digit abduction (9/10) 4 hr post dose: mild paresis (6/10), moderate paresis (3/10), decreased digit abduction (9/10) 24 hr post dose: mild paresis (8/10), decreased digit abduction (8/10) 48 hr post dose: mild paresis (8/10), decreased digit abduction (9/10) |
| Macroscopic observations at time of tissue collection |  | No signs (10/10) | Mild redness at injection site (7/10), moderate redness (1/10), no signs (2/10) | Mild redness at injection site (6/10), no signs (4/10) | Mild redness at injection site (5/10), moderate redness (1/10), no signs (4/10) | Mild redness at injection site (6/10), no signs (1/10) | Mild redness at injection site (7/10), no signs (3/10) |

Figure 4:
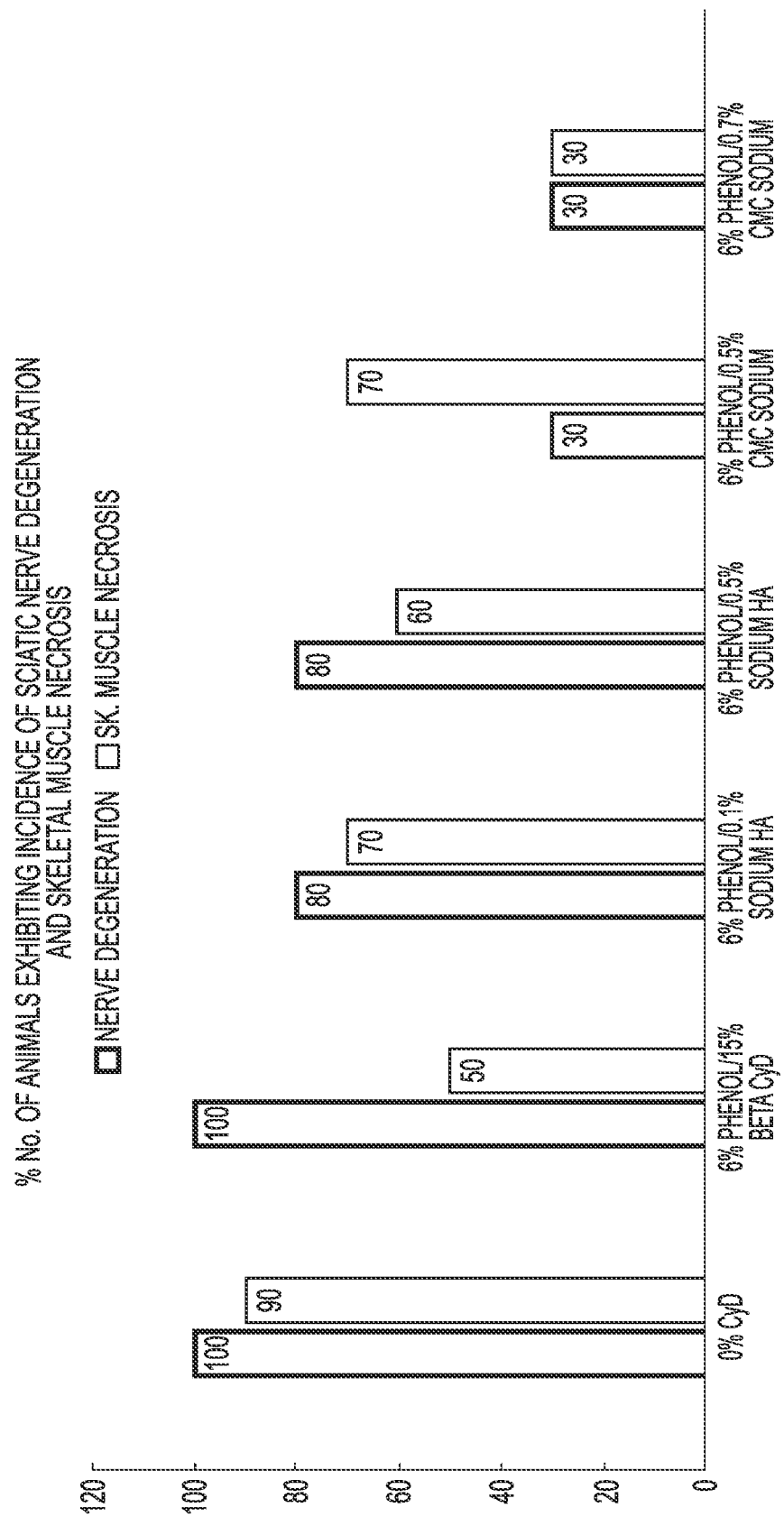
FIG. 4 compares the incidence of sciatic nerve degeneration and skeletal muscle necrosis across each group of rats when administered with 6% (w/w) phenol formulations at 15% (w/w) HP-β-CD and viscoelastic-based formulations using HA and NaCMC.

FIG. 4 compares the incidence of sciatic nerve degeneration and skeletal muscle necrosis across each group of rats when administered with the lead 6% w/w phenol formulations at 15% w/w HPβCD and the alternate viscoelastic based formulations using HA and NaCMC polymers at the two levels (shown in Table D above). In the Figure, nerve degeneration is deemed to be desirable, and skeletal muscle necrosis undesirable. Thus, the better performing formulations have the greatest difference between these results. As can be seen in FIG. 4, the viscoelastic based formulations were deemed to be inferior to the cyclodextrin based formulation with respect to sciatic nerve degeneration effects relative to the minimization of skeletal muscle necrosis.

This finding—that the cyclodextrin and its derivatives would prove to be the best of the three initial choices (in situ gelling, viscoelastic, and complexation/encapsulation) is surprising in and of itself. In this regard, the inventors initially had no particular preference or belief that one of the three possible candidate strategies would be any better than any other strategy—there were no published studies available to explain how phenol would be released or otherwise become available in vivo to interact with surrounding tissue from these formulations. In fact, if anything, the viscoelastic formulation using hyaluronic acid was probably the most attractive given that it is naturally occurring in mammals and has been used pharmaceutically as a viscosity modifying agent. There was nothing to initially suggest that complexation/encapsulation would provide a different, not to mention better, result than the other formulations.

Example 2—Dosing Studies Using Phenol and Various Cyclodextrins

Figure 2:
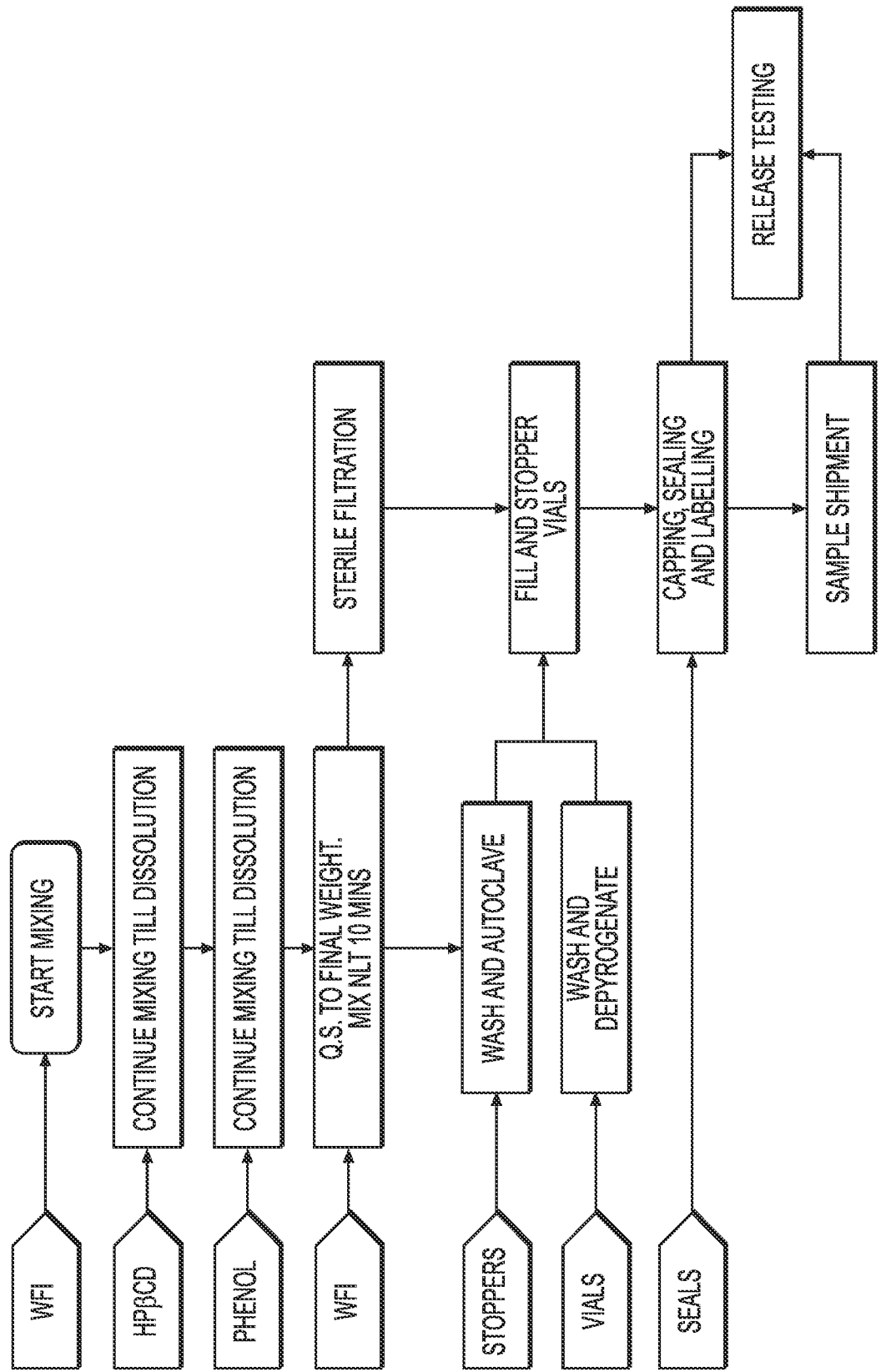
FIG. 2 is an example of a block diagram of the process used for mixing the composition used in Example 1.

The formulations presented in Table 1 and Table 3 were manufactured as per the manufacturing process outlined in FIG. 2 and then screened in a rodent sciatic nerve block model, where 0.2 mls phenol/rat was administered caudal to the sciatic notch of the pelvis in the right hind limb as a perineural injection. The dose and volume injected were selected based on data from previous sciatic nerve block studies (Reference Appendix 1 for a detailed overview of non-clinical studies and conclusions).

TABLE 1

| | Prototype | | | | |
|---|---|---|---|---|---|
| | 6% Aqueous Phenol (control) | 6% Phenol, 20% Hydroxypropyl-β Cyclodextrin | 6% Phenol, 40% Hydroxypropyl-β Cyclodextrin | 9% Phenol, 40% Hydroxypropyl-β Cyclodextrin | 6% Phenol, 20% Hydroxypropyl-γ Cyclodextrin |
| Appearance | Clear colorless solution | Clear colorless solution, free of visible particulates | Clear colorless solution, free of visible particulates | Clear colorless solution, free of visible particulates | Clear colorless solution, free of visible particulates |
| pH | 3.6 | 6.4 | 6.8 | 6.6 | 5.8 |
| Viscosity (cSt) | — | 2.8 | 13.5 | 15.7 | 2.7 |
| Osmolality (mOsm/kg) | 551 | 466 | 342 | 392 | 390 |
| Assay | 99.3% | 104.5% | 112.7% | 112.4% | 104.8% |
| Particulate matter (HIAC) | Confirms | Confirms | Confirms | Confirms | Confirms |
| ≥10 μm NMT 6000 | 366 | 64 | 92 | 31 | 90 |
| ≥25 μm NMT 600 | 18 | 1 | 29 | 12 | 0 |
| Syringe-ability (25G needle) | — | Free flowing solution during withdrawal and injection | Slow viscous withdrawal and free flowing injection | Slow viscous withdrawal and free flowing injection | Free flowing solution during withdrawal and injection |

TABLE 3

| | Prototype | | | | |
|---|---|---|---|---|---|
| | 6% Aqueous Phenol (control) | 6% Phenol, 10% Hydroxypropyl-β Cyclodextrin | 6% Phenol, 12.5% Hydroxypropyl-β Cyclodextrin | 9% Phenol, 15% Hydroxypropyl-β Cyclodextrin | 6% Phenol, 17.5% Hydroxypropyl-β Cyclodextrin |
| Appearance | Clear colorless solution | Clear colorless solution, free of visible particulates | Clear colorless solution, free of visible particulates | Clear colorless solution, free of visible particulates | Clear colorless solution, free of visible particulates |
| pH | 3.6 | 5.9 | 6.0 | 6.1 | 6.2 |
| Viscosity (cSt) | — | 1.6 | 1.8 | 2.1 | 2.3 |
| Osmolality (mOsm/kg) | 551 | 473 | 454 | 460 | 456 |
| Assay | 99.3% | 98.8% | 99.8 | 100.7 | 101.8 |
| Particulate matter (HIAC) | Confirms | Confirms | Confirms | Confirms | Confirms |
| ≥10 μm NMT 6000 | 366 | 20 | 16 | 26 | 26 |
| ≥25 μm NMT 600 | 18 | 0 | 0 | 4 | 4 |
| Syringe-ability (25G needle) | — | Free flowing withdrawal and injection | Free flowing withdrawal and injection | Free flowing withdrawal and injection | Free flowing withdrawal and injection |

The animals were observed pre-dose and at periodic intervals over a 48-hour period for target hind limb paresis, ataxia and abnormal posture. Additionally, pain measurement and motor activity were performed. Necropsy was performed on animals 48 hours post injection and target nerve and muscle tissue samples adjacent to the injection site were collected and processed for histopathological evaluation (e.g. assessment of the degree of nerve sciatic degeneration and local skeletal muscle degeneration and necrosis). Macroscopic observations of edema, erythema and irritation at the dermal site of needle insertion was also performed.

Table 2 provides a summary of the histopathological evaluation associated with formulations presented in Table 1. In summary, by the complexation of phenol with CDs (HP β and HP-γ-CDs), one can observe a noticeable reduction in the number of animals with local skeletal muscle necrosis as compared to the standard 6% aqueous phenol solution, whilst achieving effective sciatic nerve degeneration. This latter observation was matched by 'clinical' effects on the animal hind limbs, including paresis and digit abduction.

TABLE 2

| Pathology | | Number of Animals | Group 1: Water for Injection (control) | Group 2: 6% Aqueous Phenol | Group 3: 6% Phenol, 20% HP-β CD | Group 4: 6% Phenol, 40% HP-β CD | Group 5: 9% Phenol, 40% HP-β CD | Group 6: 6% Phenol, 20% HP-γ CD |
|---|---|---|---|---|---|---|---|---|
| Sciatic Nerve degeneration | Total | | 0 | 10 | 8 | 0 | 6 | 10 |
| | 1> | | 0 | 2 | 6 | 0 | 6 | 6 |
| | 2> | | 0 | 6 | 2 | 0 | 0 | 3 |
| | 3> | | 0 | 2 | 0 | 0 | 0 | 1 |
| Skeletal Muscle degeneration | Total | | 3 | 10 | 9 | 9 | 8 | 10 |
| | 1> | | 3 | 5 | 4 | 8 | 5 | 4 |
| | 2> | | 0 | 5 | 5 | 1 | 2 | 4 |
| | 3> | | 0 | 0 | 0 | 0 | 1 | 2 |
| Necrosis | Total | | 0 | 9 | 4 | 1 | 3 | 7 |
| | 1> | | 0 | 5 | 2 | 1 | 2 | 2 |
| | 2> | | 0 | 4 | 2 | 0 | 0 | 5 |
| | 3> | | 0 | 0 | 0 | 0 | 1 | 0 |
| Clinical Signs | | | No signs from 1-48 hours | 1 hr post dose: mild paresis (8/10), moderate paresis (2/10), decreased digit abduction (10/10) 4-48 hr post dose: mild paresis (9/10), moderate paresis, decreased digit abduction (10/10) | 1-4 hr post dose: mild paresis (9/10), decreased digit abduction (9/10) 24-48 hr post dose: mild paresis (8/10), decreased digit abduction (8/10) | 1-4 hr post dose: slight paresis (1/10), 24-48 hr post dose: no signs | 1 hr post dose: mild paresis (4/10), moderate paresis (1/10), slight paresis (1/10), decreased digit abduction (5/10), intermittent twitching (1/10) 4 hr post dose: mild paresis (5/10), slight paresis (2/10), decreased digit abduction (5/10) 24-48 hr. post dose: mild paresis (5/10), decreased digit abduction (5/10) | mild paresis (10/10), decreased digit abduction (10/10) |
| Macroscopic observations at time of tissue collection | | | No signs (10/10) | Mild redness at injection site (7/10), moderate redness (1/10), no signs (2/10) | Mild redness at injection site (6/10), moderate redness (1/10), no signs (3/10) | Mild redness at injection site (2/10), no signs (8/10) | Mild redness at injection site (2/10), moderate redness (1/10), no signs (6/10) | Mild redness at injection site (8/10), no signs (2/10) |

Table 4 below provides a summary of the histopathological evaluation associated with formulations manufactured with incremental increases in the dose level of HP β CD from 10% w/w to 17.5% w/w (Refer to Table 3) based on the learnings from the initial prototype screen as outlined in Table 2.

TABLE 4

| Pathology | | Number of Animals | Group 1: Water for Injection | Group 2: 6% Aqueous Phenol (active control) | Group 3: 6% Phenol, 10% HP-β CD | Group 4: 6% Phenol, 12.5% HP-β CD | Group 5: 6% Phenol, 15% HP-β CD | Group 6: 6% Phenol, 17.5% HP-β CD |
|---|---|---|---|---|---|---|---|---|
| Sciatic Nerve degeneration | Total | | 0 | 10 | 10 | 10 | 10 | 10 |
| | 1> | | 0 | 2 | 2 | 0 | 3 | 3 |
| | 2> | | 0 | 6 | 4 | 4 | 2 | 4 |
| | 3> | | 0 | 2 | 4 | 6 | 5 | 3 |
| Skeletal Muscle degeneration | Total | | 3 | 10 | 7 | 7 | 9 | 9 |
| | 1> | | 3 | 5 | 7 | 6 | 8 | 9 |
| | 2> | | 0 | 5 | 0 | 1 | 1 | 0 |
| Necrosis | Total | | 0 | 9 | 9 | 7 | 5 | 6 |
| | 1> | | 0 | 5 | 0 | 3 | 0 | 0 |
| | 2> | | 0 | 4 | 2 | 2 | 1 | 5 |
| | 3> | | 0 | 0 | 7 | 2 | 4 | 1 |
| Clinical Signs | | | No signs from 1-48 hours | 1 hr post dose: mild paresis (8/10), moderate paresis (2/10), decreased digit abduction (10/10) | 1 hr post dose: mild paresis (6/10), moderate paresis (3/10), decreased digit abduction (9/10) | 1 hr post dose: mild paresis (6/10), moderate paresis (3/10), decreased digit abduction (9/10) 4-24 hr post | 1 hr post dose: slight paresis (1/10), mild paresis (7/10), moderate paresis (2/10), decreased digit | 1 hr post dose: mild paresis (7/10), moderate paresis (2/10), decreased digit abduction (9/10) 4-24 hr post dose: mild |

TABLE 4-continued

| Pathology | Number of Animals | Group 1: Water for Injection | Group 2: 6% Aqueous Phenol (active control) | Group 3: 6% Phenol, 10% HP-β CD | Group 4: 6% Phenol, 12.5% HP-β CD | Group 5: 6% Phenol, 15% HP-β CD | Group 6: 6% Phenol, 17.5% HP-β CD |
|---|---|---|---|---|---|---|---|
| | | | 4-48 hr post dose: mild paresis (9/10), moderate paresis, decreased digit abduction (10/10) | 4-48 hr post dose: mild paresis (8/10), moderate paresis (1/10), decreased digit abduction (9/10) | dose: mild paresis (7-8/10), moderate paresis (1-2/10), decreased digit abduction (9/10) | abduction (9/10) 4-24 hr post dose: slight paresis (1/10), mild paresis (8/10), moderate paresis, (1/10), decreased digit abduction (9/10) 48 hr post dose: mild paresis (8/10), decreased digit abduction (8/10) | paresis (8/10), moderate paresis (1/10), decreased digit abduction (9/10) 24-48 hr post dose: mild paresis (8-9/10), decreased digit abduction (8-9/10) |
| Macroscopic observations at time of tissue collection | | No signs (10/10) | Mild redness at injection site (7/10), moderate redness (1/10), no signs (2/10) | Mild redness at injection site (6/10), moderate redness (1/10), no signs (3/10) | Mild redness at injection site (5/10), severe redness (1/10), no signs (3/10) | Mild redness at injection site (9/10), no signs (1/10) | Mild redness at injection site (6/10), moderate redness (2/10), no signs (2/10) |

Figure 3:
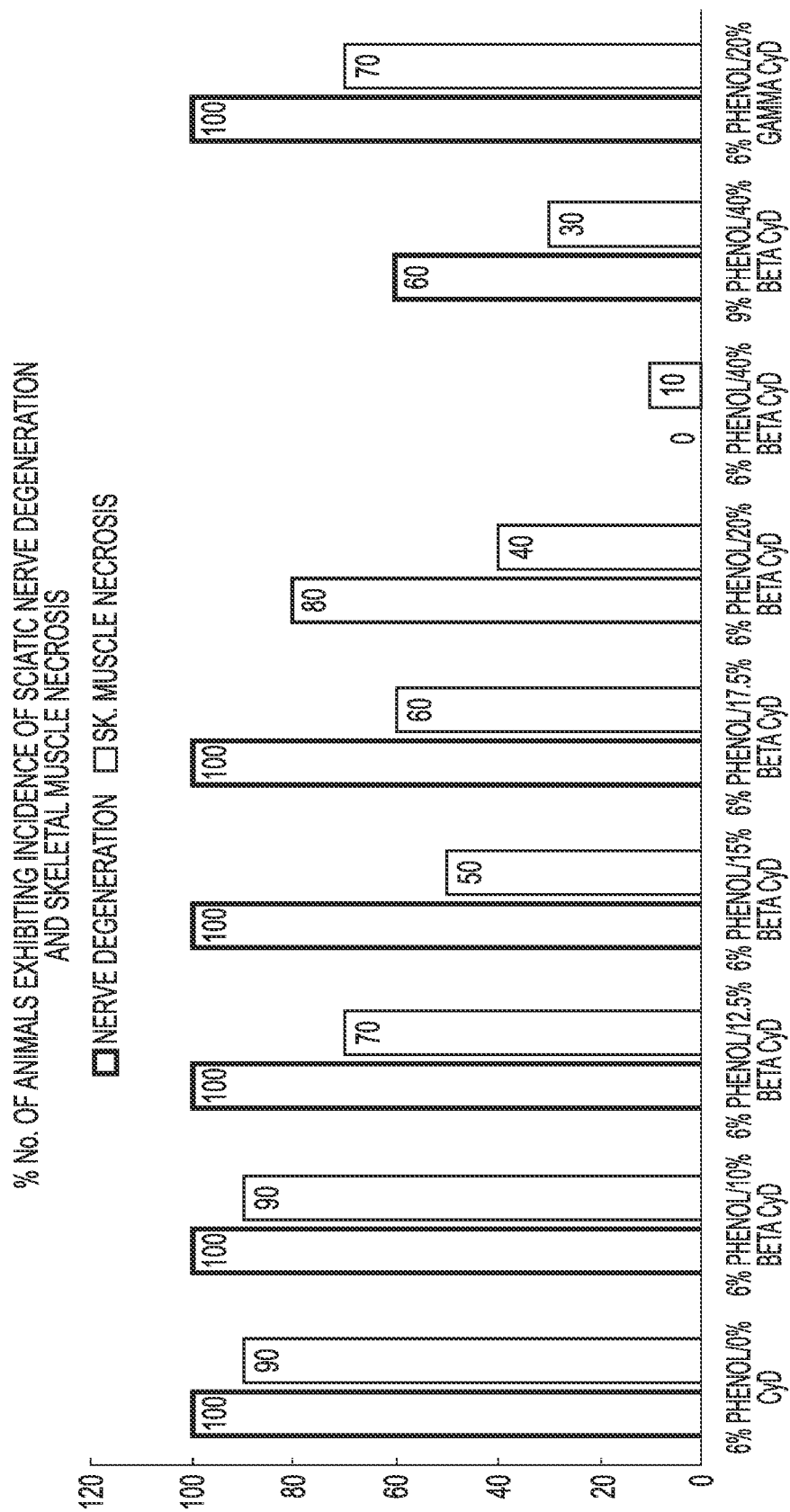
FIG. 3 summarizes the data from animal studies with a range of cyclodextrin compositions.

One can observe a noticeable reduction in the number of animals with local skeletal muscle necrosis between the range of 15-17.5% w/w HP β CD as compared to the standard 6% aqueous phenol solution without complexing agent, whilst achieving effective sciatic nerve degeneration. There is a dose-dependent relationship observed where the number of animals exhibiting muscle necrosis increases as the level of HP β CD decreases below 12.5% w/w (see FIG. 3).

A surprising observation from the histopathology data was that at comparable % (w/w) CD to phenol, the 20% HP β. CD and 20% HP-γ-CD resulted in different therapeutic improvement effects. Another surprising observation was that an increase in % CD (w/w) to phenol from 20% to 40% had a dramatic effect in reducing efficacy but improving local safety. A further surprising effect was that increasing the free fraction of phenol for the 20% HP β CD (9% total phenol) did not match the standard 6% phenol effect but did show some signs of systemic toxicity.

Example 3—Further Studies Using Phenol and Cyclodextrin

Further studies were performed to evaluate various other dosing considerations. The details and results of the studies are summarized in Table 5 below.

Briefly, for the studies summarized in Table 5 below, all were single dose perineural injection studies in Sprague Dawley rats, which consisted of 8 to 10 animals per group. Animals were dosed with solutions of phenol and vehicle (supplied by Alcami Corporation, 2320 Scientific Park Dr., Wilmington, N.C. 28405). Sterile water for injection (WFI) was used as a vehicle control for these studies.

Clinical observations were made at pre-dose and 1, 4, 24, and 48 hours after dosing for paresis, ataxia and abnormal posture. Observations were made at ±5 minutes for the 1-hour post-dose observations and ±15 minutes for the later observations. The pain threshold of the hind paw of the injected side was measured immediately following the clinical observations at approximately 1, 4, 24, and 48 hours after dosing. Animals were then placed in a photobeam activity system at approximately 1, 4, 24, and 48 hours post dose for 5 minutes to assess spontaneous motor activity. A necropsy was performed and nerve and muscle tissue samples adjacent to the injection site were collected and processed for histopathological evaluation. The collected tissues were preserved in 10% neutral buffered formalin (NBF) and evaluated for histopathological changes.

TABLE 5

| Study Title | Objective/Description | Dose | Duration | Results |
|---|---|---|---|---|
| Effect of Phenol Administered Perineurally on Sciatic Nerve Function in Rats | To identify the preferred volume to be used in the perineural injection caudal to the sciatic notch of the hind limb | 60 mg/mL aqueous Phenol @ 0.1, 0.2, 0.3, 0.4 and 0.5 mL/rat | 48 hrs | Injection volume ovar 0.2 mL saturates the tissue peripheral to the target site. All subsequent studies focused on a volume of 0.2 mL |
| Effect of Phenol Administered Perineurally on Sciatic Nerve Function in Rats | To evaluate the target dose range to be used in the perineural injection caudal to the sciatic notch of the hind limb | 60 mg/mL, and 75 mg/mL aqueous Phenol @ 0.2 mL/rat | 48 hrs | No significant dose-dependent effects were observed across the range assessed |
| A Four Week Study of Sciatic Nerve Function After a Single Perineural Injection of Aqueous Phenol Solution in Rats | To evaluate the preferred dose and injection volume to produce an effective block of the sciatic nerve function and to assess the effects of the nerve block on the sciatic nerve function and surrounding tissue ovar this 28 day period | 60 mg/mL aqueous Phenol @ 0.2 mL/rat | 28 days | Over 28 days, time-dependent microscopic alterations in the sciatic nerve and skeletal muscle tissues Myofascial inflammation/fibroplasia/granulation tissue with or without subjacent myofiber regeneration was noted through Day 21, with complete recovery by Day 28 Sciatic nerve fibroplasia/inflammation/hemorrhage (epineurial) with pronounced axonal degeneration and regeneration were present on Day 7, with total resolution of the epineurial alterations and ongoing recovary of the axonal effects noted by Day 28 |
| Effect of Phenol Formulations Administered Perineurally on Sciatic Nerve Function in Rats | To evaluate the ability of four phenol prototype formulations administered by perineural injection to evaluate its ability to block the sciatic nerve function. | 6% (60 mg/ml) aqueous phenol solution 6% (60 mg/g or 64 mg/ml) phenol prepared in 20% HPβCD solution 6% (60 mg/g or 68.4 mg/ml) phenol prepared 40% HPβCD solution 9% (90 mg/g or 102.4 mg/ml) of phenol prepared in 40% HPβCD solution and 6% (60 mg/g or 64.2 mg/ml) of phenol prepared in 20% HPγCD solution | 48 hrs | 6% Phenol/20% HPβCD formulation demonstrated enhanced safety profile with comparable clinical effect as reported from the histopathologic analysis of the animal tissues The degree of sciatic nerve degeneration and skeletal muscle degeneration was comparable however there was a significant reduction in the number of animals with reported skeletal muscle necrosis |

TABLE 5-continued

| Study Title | Objective/Description | Dose | Duration | Results |
|---|---|---|---|---|
| Effect of Phenol Formulations Administered Perineurally on Sciatic Nerve Function in Rats - Study 2 | To evaluate the ability of four phenol prototype formulations (with varying concentrations of HPβCD (10-17.5%) administered by perineural injection to evaluate its ability to block the sciatic nerve function. | 6% (60 mg/g or 63 mg/ml) phenol/(10%) 103.2 mg/ml HPβCD solution<br>6% (60 mg/g or 63 mg/ml) phenol/(15%) 157.4 mg/ml HPβCD solution<br>6% (60 mg/g or 63 mg/ml) phenol/(17.5%) 184.9 mg/ml HPβCD solution<br>6% (60 mg/g or 63 mg/ml) phenol/(12.5%) 130.1 mg/ml HPβCD solution | 48 hrs | Each formulation caused mild to moderate paresis Degeneration and inflammation with less frequent hemorrhage were noted in the sciatic nerves while myofiber necrosis/degeneration usually accompanied by inflammatory cell infiltrates, edema, and hemorrhage was present in skeletal muscle<br>A slight increase in the incidenceIntensity of myofiber necrosis in the skeletal muscle was observed in animals injected with 63 mg/mL phenol solution/10% HPβCD solution, as compared to the other test article treatment groups<br>Based on the results from previous studies, formulation of 6% (63 mg/mL) Phenol prepared in 15% (157.4 mg/mL) HPβCD solution is planned to use in future studies based on reported sciatic nerve degeneration whilst minimizing skeletal muscle necrosis and skeletal muscle degeneration. |
| Effect of Phenol Formulations Administered Perineurally on Sciatic Nerve Function in Rats | To evaluate the ability of several phenol viscoelastic formulations administered by perineural injection to evaluate its ability to Study 3 block the sciatic nerve function. | 6% (60 mg/g or 60.3 mg/ml) phenol/0.1% w/w Sodium hyaluronate<br>6% (60 mg/g or 60.3 mg/ml) phenol/0.5% w/w Sodium hyaluronate<br>6% (60 mg/g or 60.3 mg/ml) phenol/0.5% w/w Carboxymethylcellulose sodium<br>6% (60 mg/g or 60.4 mg/ml) phenol/0.7% w/w Carboxymethylcellulose sodium | 48 hrs | The perineural administration of the injected 6% w/w phenol/0.1% w/w Sodium hyaluronate solution and 6% w/w phenol/0.7% w/w Carboxymethylcellulose sodium caused mild to moderate paresis and decreased digit abduction in most animals at all timepoints. Incidence of clinical signs after perineural administration appeared to be lower with 6% w/w phenol/0.5% w/w Sodium hyaluronate solution or 6% w/w phenol/0.5% w/w Carboxymethylcellulose sodium.<br>Microscopic examination of injection sites post injection revealed test article minimal to moderate focal segmental degeneration of sciatic nerve axons and focal monophasic degeneration and necrosis of skeletal muscle fibers with a secondary inflammatory response in all groups receiving test articles. Axon degeneration and myofiber degeneration and necrosis were modestly reduced in incidence among rats receiving the 6% w/w phenol/0.7% w/w Carboxymethylcellulose sodium as compared to the other three treatment groups. |

The present disclosure includes any combination of these various features or embodiments above and/or below as set forth in sentences and/or paragraphs. Any combination of disclosed features herein is considered part of the present disclosure and no limitation is intended with respect to combinable features.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the disclosure be limited to the specific values recited when defining a range.

Other embodiments of the present disclosure will be apparent to those skilled in the art from consideration of the present specification and practice of the present disclosure disclosed herein. It is intended that the present specification and examples be considered as exemplary only with a true scope and spirit of the disclosure being indicated by the following claims and equivalents thereof.

REFERENCES

1. Brewster Me. and Loftsson T (2007) Cyclodextrins as pharmaceutical solubilizers. Advanced Drug 143, Delivery Reviews 59: 645-666.
2. Lin, S-Fen and Kenneth, C. A (1983) Complex Formation Between α-Cyclodextrin and 4-Substituted Phenols Studied by Potentiometric and Competitive Spectrophotometric Methods. Journal of Pharmaceutical Sciences. 72 (11), 1333-1338.
3. Yin, Q., Li, J., Zheng, Q., Yang, X., Rong Lv1, Ma, L., Liu, J., Zhu, T and Zhang, W. The quaternary lidocaine derivative QX-314 in combination with bupivacaine for long-lasting nerve block: Efficacy, toxicity, and the optimal formulation in rats. PLoS One. 2017; 12(3): e0174421.
4. Wang, Z., Huang, H., Yang, S., Huang, S., Guo, J., Tang, Q. and Qi, F. Long-term effect of ropivacaine nanoparticles for sciatic nerve block on postoperative pain in rats. Int. J. Nanomed. 2016:11 2081-2090.
5. Loyd D R, Chen P B, Hargreaves K M. Anti-hyperalgesic effects of anti-serotonergic compounds on serotonin- and capsaicin-evoked thermal hyperalgesia in the rat. Neuroscience. 2012 Feb. 17; 203:207-15. doi: 10.1016/j.neuroscience.2011.12.019. Epub 2011 Dec. 20.
6. Liu X J, White T D, Sawynok J. Intraplantar injection of glutamate evokes peripheral adenosine release in the rat hind paw: involvement of peripheral ionotropic glutamate receptors and capsaicin-sensitive sensory afferents. J Neurochem. 2002 February; 80(4):562-70.
7. Lin C C, et al. Optimal effect of Phenol in Sciatic Nerve. Chinese Journal of Physiology 2015; 58 (4): 237-243.
8. Szente, Lajos, Szejtli J and Kis, G. L. Spontaneous Opalescence of Aqueous γ-Cyclodextrin Solutions: Complex Formation or Self-Aggregation? Journal of Pharmaceutical Sciences 1998: 87(6): 778-781.

What is claimed is:

1. A method for creating a nerve-block in a mammal comprising:
   administering an effective amount of a phenol formulation, the formulation consisting of phenol,
   a cyclodextrin or derivative thereof complexing at least a portion of the phenol,
   at least one pharmacologically acceptable solvent for administration,
   at least one dye or other agent to provide for visual localization of the phenol formulation, and
   optionally one or more pharmaceutically acceptable excipients.

2. The method according to claim 1, wherein the administering is by injection.

3. The method according to claim 1, wherein the administering is by topical application.

4. The method according to claim 1, wherein the cyclodextrin is hydroxypropyl-β-cyclodextrin (HP-β-CD).

5. The method according to claim 4, wherein the concentration of the hydroxypropyl-β-cyclodextrin in the formulation is from about 10% to about 20% by weight (w/w) of the formulation.

6. The method according to claim 5, wherein the concentration of the hydroxypropyl-β-cyclodextrin is from about 12% to about 18% by weight (w/w) of the formulation.

7. The method according to claim 6, wherein the concentration of the phenol in the formulation is from about 3% to about 9% by weight (w/w) of the formulation.

8. The method according to claim 7, wherein the concentration of the phenol is about 6% by weight (w/w) of the formulation.

9. The method according to claim 1, the method further comprising visualizing the phenol formulation.

10. The method according to claim 9, wherein the visualizing is performed by ultrasound, electronic stimulation, fluoroscopy, or camera.

11. A method for treating therapeutic, cosmetic, or tissue lysis condition in a patient in need thereof, comprising:
    injecting into or applying in proximity of a physiological target area in proximity to or within a nerve, blood vessel, tumour, or tissue growth of the patient an effective amount of a phenol formulation, the formulation consisting of:
    phenol,
    a cyclodextrin or derivative thereof complexing at least a portion of the phenol,
    at least one pharmacologically acceptable solvent for injection,
    at least one dye or other agent to provide for visual localization of the phenol formulation, and
    optionally one or more pharmaceutically acceptable excipients.

12. The method according to claim 11, wherein the phenol formulation comprises from about 3% to about 9% by weight phenol, and from about 10% to about 20% by weight cyclodextrin or derivative.

13. A method for creating a nerve-block in a mammal comprising:
    administering an effective amount of a phenol formulation, the formulation consisting of phenol,
    a cyclodextrin or derivative thereof complexing at least a portion of the phenol,
    at least one pharmacologically acceptable solvent for administration, and
    optionally one or more pharmaceutically acceptable excipients; and further comprising administering at least one dye or other agent to provide for visual localization of the phenol formulation.

14. The method according to claim 13, wherein the at least one dye or other agent is administered concurrently with the phenol formulation.

15. The method according to claim 13, wherein the at least one dye or other agent is administered before the phenol formulation.

16. The method according to claim 13, wherein the at least one dye or other agent is administered after the phenol formulation.

17. The method according to claim 1, wherein the administering is made into an intra-articular space.

18. The method according to claim 1, wherein the administering is made into a joint.

19. The method according to claim 1, wherein the administering is post-surgical.

\* \* \* \* \*